(12) United States Patent
Kuklish et al.

(10) Patent No.: US 8,252,831 B2
(45) Date of Patent: Aug. 28, 2012

US008252831B2

(54) IMIDAZOLE-2-BENZAMIDE COMPOUNDS USEFUL FOR THE TREATMENT OF OSTEOARTHRITIS

(75) Inventors: Steven Lee Kuklish, Fishers, IN (US); Matthew Allen Schiffler, Indianapolis, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/327,803

(22) Filed: Dec. 16, 2011

(65) Prior Publication Data

US 2012/0157506 A1 Jun. 21, 2012

Related U.S. Application Data

(60) Provisional application No. 61/425,478, filed on Dec. 21, 2010.

(51) Int. Cl.
*A61K 31/4168* (2006.01)
*C07D 233/88* (2006.01)
(52) U.S. Cl. .................. 514/398; 548/326.5
(58) Field of Classification Search ............... 548/326.5; 514/398
See application file for complete search history.

(56) References Cited

U.S. PATENT DOCUMENTS

| 2010/0081643 A1 | 4/2010 | Bookser et al. |
| 2010/0324086 A1 | 12/2010 | Wannberg et al. |
| 2011/0275656 A1 | 11/2011 | Pfau et al. |
| 2011/0312935 A1 | 12/2011 | Pfau et al. |
| 2012/0108583 A1 | 5/2012 | Gharat et al. |

FOREIGN PATENT DOCUMENTS

| WO | 2007124589 | 11/2007 |
| WO | 2009103778 | 8/2009 |
| WO | WO-2009/103778 A1 * | 8/2009 |
| WO | 2010034798 | 4/2010 |
| WO | 2010100249 | 9/2010 |
| WO | 2010127152 | 11/2010 |
| WO | 2011048004 | 4/2011 |

OTHER PUBLICATIONS

Samuelsson, et al., "Membrane Prostaglandin E Synthase-1: A Novel Therapeutic Target," The Americal Society of Pharmacology and Experimental Therapeutics, vol. 59, No. 3, pp. 207-224 (2007).

Iyer, et al., "Prostaglandin E2 synthase inhibition as a therapeutic target," Expert Opinion Therapeutic Targets, vol. 13, No. 7, pp. 849-865 (2009).
Wang, et al., "Prostaglandin E2 synthase-1 inhibition in cardiovascular inflammatory disease," Journal of Internal Medicine, vol. 263, pp. 500-505 (2008).
Cote, et al., "Substituted phananthrene imidazoles as potent, selective, and orally active mPGES-1 inhibitiors," Bioorganic & Medicinal Chemistry Letters, vol. 17, pp. 6816-6820 (2007).
Trebino, et al., "Impaired inflammatory and pain responses in mice lacking an inducible prostaglandin E synthase," Proc. Natl. Acad. Sci., vol. 100, No. 15, pp. 9044-9049 (2003).
Warner, et al., "Nonsteroid drug selectivities for cyclo-oxygenase-1 rather than cyclo-oxygenase-2 are associated with human gastrointestinal toxicity: A full in vitro analysis," Proc. Natl. Acad. Sci., vol. 96, pp. 7563-7568 (1999).
San Juan, et al., "3D-QSAR study of mircrosomal prostaglandin E2 synthase (mPGES-1) inhibitors," J. Mol. Model, vol. 13, pp. 601-610 (2007).
Huntjens, et al., "Pharmacokinetic-pharmacodynamic correlations and biomarkers in the development of COX-2 inhibitors," Rheumatology, vol. 44, pp. 846-859 (2005).
Brideau, et al., "A human whole blood assay for clinical evaluation of biochemical efficacy of cyclooxygenase inhibitors," Inflamm Res., vol. 45, pp. 68-74 (1996).

* cited by examiner

*Primary Examiner* — Kamal Saeed
*Assistant Examiner* — Janet L Coppins
(74) *Attorney, Agent, or Firm* — James B. Myers

(57) ABSTRACT

The present invention provides compounds of the formula below

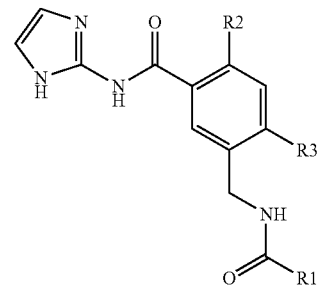

or pharmaceutical salts thereof, wherein R1, R2 and R3 are as described herein; methods of treating osteoarthritis using the compounds; and a process for preparing the compounds.

11 Claims, No Drawings

IMIDAZOLE-2-BENZAMIDE COMPOUNDS USEFUL FOR THE TREATMENT OF OSTEOARTHRITIS

Osteoarthritis is a complex degenerative disease of joints characterized by progressive destruction of articular cartilage and peri-articular structures including bones, synovium, and associated fibrous joint tissues, and varying degrees of inflammation. Existing drug therapies can reduce pain associated with osteoarthritis, but may be only moderately effective over time and such therapies have a variable risk/benefit consideration. Current treatments using non-steroidal, anti-inflammatory drugs (NSAIDS) and/or Cyclooxygenase-2 inhibitors (COX-2 inhibitors) are efficacious, but can cause significant cardiovascular and gastrointestinal effects. Consequently these classes of drugs may be contraindicated for many patients due to the patient's pre-existing or emergent cardiovascular and/or gastrointestinal conditions. Additionally, patients on these therapies can become refractory to specific drug treatments.

Prostaglandin $E_2$, is produced through the metabolism of arachidonic acid by the cyclooxygenases to generate the unstable intermediate prostaglandin $H_2$ ($PGH_2$). Prostaglandin $H_2$ is then further metabolized by microsomal prostaglandin $E_2$ synthase-1 (mPGES-1) to $PGE_2$. Prostaglandin E2 is an important mediator of conditions associated with osteoarthritis, for example, fever, pain, and inflammation.

There remains a need for additional options to treat and alleviate pain and/or inflammation associated with osteoarthritis. The present invention provides novel inhibitors of mPGEs-1 inhibitors and may be beneficial for treating patients suffering from the pain and/or inflammation of osteoarthritis.

Publication WO 2011048004 discloses compounds of Formula Ic illustrated below

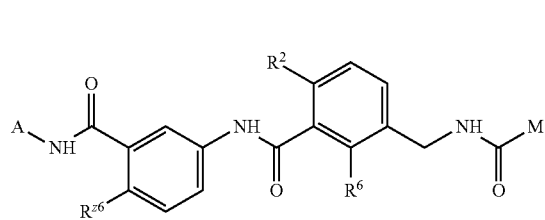

Ic where A, M, $R^{z6}$, $R^2$ and $R^6$ are as described therein and are listed as useful in prevention and/or treatment of a disease in which the inhibition of mPGES-1 is a therapeutic benefit.

The present invention provides compounds of the formula I:

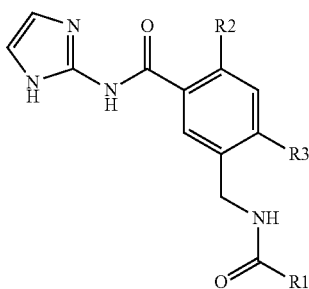

I wherein R1 is selected from: —$C_{1-5}$ alkyl, —$C(CH_3)_2$ ($OCH_3$), —$C(CF_3)$-cyclopropyl and —$C(CH_3)$-cyclopropyl; $R^2$ is selected from: halo, —$CH_3$, —$CF_3$, and —$CHF_2$; and $R^3$ is selected from: H, halo, and —$CH_3$; or pharmaceutically acceptable salts thereof.

The present invention provides compounds of Formula I or pharmaceutically acceptable salts thereof, wherein R1 preferably is selected from: —$C(CH_3)_3$, —$CH(CH_3)_2$, —$C(CH_3)_2$ ($OCH_3$), —$C(CF_3)$-cyclopropyl, and —$C(CH_3)$-cyclopropyl. More preferably R1 is —$C(CH_3)_3$ or —$CH(CH_3)_2$.

The present invention provides compounds of Formula I or pharmaceutically acceptable salts thereof, wherein R2 is selected from Br, Cl, —$CH_3$, —$CF_3$, and —$CHF_2$. More preferably R2 is selected from: Cl, —$CF_3$, and —$CHF_2$. Still more preferably R2 is Cl.

The present invention provides compounds of Formula I or pharmaceutically acceptable salts thereof wherein R3 is selected from: H, F, and —$CH_3$. More preferably R3 is H or —$CH_3$. Still more preferably R3 is H.

The present invention also provides compounds of Formula I or pharmaceutically acceptable salts thereof, wherein R1 is selected from: —$C_{1-5}$ alkyl, —$C(CH_3)_2(OCH_3)$, —$C(CF_3)$-cyclopropyl and —$C(CH_3)$-cyclopropyl; and R2 is selected from: Br, Cl, —$CH_3$, —$CF_3$, and —$CHF_2$. More preferably R2 is Cl, —$CF_3$, and —$CHF_2$. Still more preferably R2 is Cl.

The present invention also provides compounds of Formula I or pharmaceutically acceptable salts thereof, wherein R1 is selected from: —$C_{1-5}$ alkyl, —$C(CH_3)_2(OCH_3)$, —$C(CF_3)$-cyclopropyl and —$C(CH_3)$-cyclopropyl; R2 is selected from: halo, —$CH_3$, —$CF_3$, and —$CHF_2$ and R3 is H, F, and —$CH_3$. More preferably R3 is selected from H or —$CH_3$; still more preferably R3 is H.

The present invention also provides compounds of Formula I or pharmaceutically acceptable salts thereof, wherein R1 is selected from: —$C(CH_3)_3$, —$CH(CH_3)_2$, —$C(CH_3)_2$ ($OCH_3$), —$C(CF_3)$-cyclopropyl, and —$C(CH_3)$-cyclopropyl; R2 is selected from: Br, Cl, —$CH_3$, —$CF_3$, and —$CHF_2$ and R3 is selected from: H, halo, and —$CH_3$. More preferably R3 is selected from H, F, and —$CH_3$. Still more preferably R3 is selected from H or —$CH_3$; still yet more preferably R3 is H.

The present invention also provides compounds of Formula I or pharmaceutically acceptable salts thereof, wherein R1 is selected from: —$C(CH_3)_3$, —$CH(CH_3)_2$, —$C(CH_3)_2$ ($OCH_3$), —$C(CF_3)$-cyclopropyl, and —$C(CH_3)$-cyclopropyl; R2 is selected from: Cl, —$CF_3$, and —$CHF_2$; and R3 is H or —$CH_3$; still yet more preferably R3 is H.

The present invention also provides a compound of Formula II:

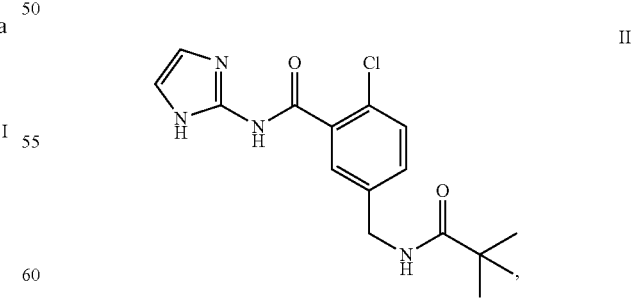

II or a pharmaceutically acceptable salt thereof.

The present invention provides a compound of Formula I or II or a pharmaceutically acceptable salt thereof wherein and at least one of a pharmaceutically acceptable carrier, diluent or excipient.

The present invention provides a method of treating a patient for pain and/or inflammation associated with osteoarthritis. The method comprises administering to the patient in need an effective amount of a compound according to Formula I or II, or a pharmaceutically acceptable salt thereof. In one form the method is for treating a patient for pain from osteoarthritis. In another form the method is for treating a patient for inflammation from osteoarthritis.

The present invention also provides a compound according to Formula I or II, or a pharmaceutically acceptable salt thereof, for use as a medicament.

The present invention provides a compound of Formula I or II or a pharmaceutically acceptable salt thereof, for use in therapy.

The present invention provides a compound of Formula I or II, or a pharmaceutically acceptable salt thereof, for use in the treatment of pain and/or inflammation associated with osteoarthritis. More preferably the present invention provides a compound of Formula I or II, or a pharmaceutically acceptable salt thereof, for use in the treatment of pain and/or inflammation from an osteoarthritis condition or associated with an osteoarthritis condition.

The phrase "pharmaceutically acceptable salt" refers to salts of the compounds of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

A "patient" refers to a mammal, preferably a human.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I, or salts thereof. The products of each step in the Schemes below can be recovered by conventional methods, including extraction, evaporation, precipitation, chromatography, filtration, trituration, and crystallization.

Additionally, the intermediates described in the following Schemes contain a number of protecting groups. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*.

The abbreviations used herein are defined according to Aldrichimica Acta, Vol. 17, No. 1, 1984. Other abbreviations are defined as follows: "Prep" refers to preparation; "Ex" refers to example; "min" refers to minute or minutes; "kPaG" refers to kilopascal Gauge; "BOP" refers to benzotriazol-1-yl-oxy-tris(dimethylamino)phosphonium hexafluorophosphate; "DIPEA" refers to diisopropylethylamine; "DCC" refers to dicyclohexylcarbodiimide; "DIC" refers to diisopropylcarbodiimide; "DMAP" refers to dimethylaminopyridine; "DMF" refers to dimethylformamide; "DMSO" refers to dimethylsulfoxide; "EDCI" refers to 1-ethyl-3-(3-dimethylaminopropyl) carbodiimide; "Et$_2$O" refers to diethyl ether; "EtOAc" refers to ethyl acetate; "HATU" refers to 2-(1H-7-azabenzotriazol-1-yl)-1,1,3,3-tetramethyl uronium hexafluorophosphate methanaminium; "HBTU" refers to O-benzotriazole-N,N,N',N'-tetramethyl-uronium-hexafluoro-phosphate; "HOAt" refers to 1-hydroxy-7-azabenzotriazole; "HOBt" refers to N-hydroxylbenzotriazole; "MeOH" refers to methyl alcohol or methanol; "PyBOP®" refers to benzotriazol-1-yloxytripyrrolidino-phosphonium hexafluorophosphate; "TBTU" refers to o-benzotriazol-1-yl-N,N,N'N'-tetramethyluronium tetrafluoroborate; "TFA" refers to trifluoroacetic acid; "THF" refers to tetrahydrofuran; "IC$_{50}$" refers to the concentration of an agent that produces 50% of the maximal inhibitory response possible for that agent; "EDTA" refers to ethylenediaminetetraacetic acid.

In the Schemes below, all substituents, unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

Scheme A

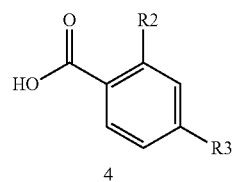

4

Step 1a

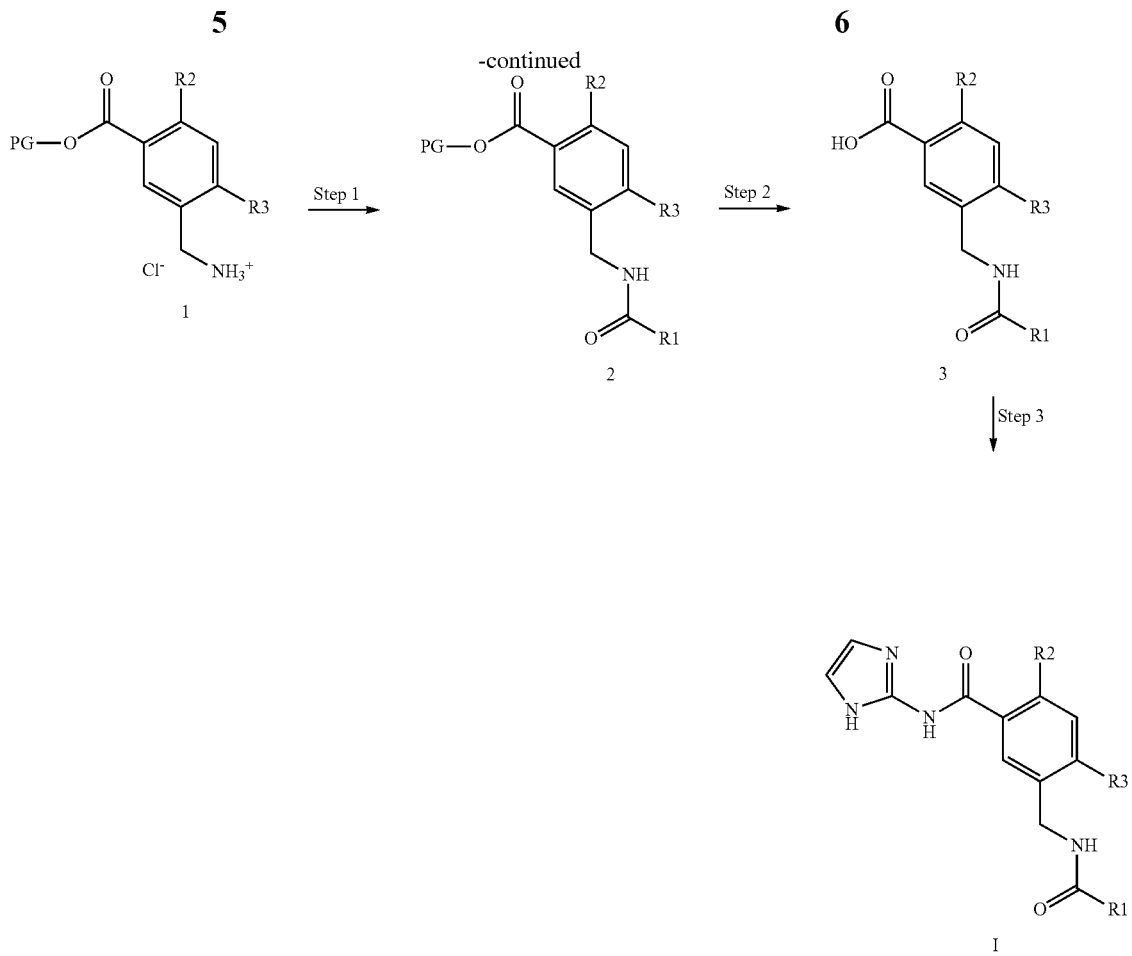

PG = protecting group

A compound of Formula I can be prepared in accordance with reactions as depicted in Scheme A. Scheme A depicts two variations to prepare compounds of Formula I. Step 1 shows the acylation of the benzylamine 1 to the amide. Following deprotection of the ester in Step 2, a coupling of a 2-aminoimidazole and a substituted benzoic acid is accomplished to give compounds of Formula 1. Step 1a shows the selective alkylation of the substituted benzoic acid followed by a coupling reaction to give compounds of Formula I. "PG" is a protecting group developed for an acid such as esters and also for an amino group such as carbamates and amides. Such protecting groups are well known and appreciated in the art, supra.

In Step 1, the benzylamine can be acylated using an acid chloride in the presence of a base such as triethylamine, N,N-diisopropylethylamine, or pyridine in an aprotic solvent such as dichloromethane or THF to give the desired amide. Alternatively, the benzylamine can be acylated with an appropriate carboxylic acid using a coupling agent. One skilled in the art will recognize that there are a number of methods and reagents for amide formation resulting from the reaction of carboxylic acids and amines. For example, the reaction of an appropriate compound 1 with an appropriate acid in the presence of a coupling reagent and an amine base, such as DIEA or triethylamine, will give a compound of formula 2. Coupling reagents include carbodiimides such as DCC, DIC, EDCI, and aromatic oximes, such as HOBt and HOAt. Additionally, uronium or phosphonium salts of non-nucleophilic anions, such as HBTU, HATU, BOP, PyBOP®, and TBTU can be used in place of the more traditional coupling reagents. Additives such as DMAP may be used to enhance the reactions.

In Step 2, the protected benzoic acid can be deprotected typically under basic conditions using an aqueous base such as lithium hydroxide or sodium hydroxide and the resulting salt acidified with an aqueous acid such as hydrochloric acid.

Step 3 illustrates the coupling of the benzoic acid with a 2-aminoimidazole. Typical coupling conditions are described in Scheme A, Step 1, and use standard coupling reagents known to those of skill in the art to give compounds of Formula I.

Alternatively, Step 1a illustrates alkylation of the substituted benzoic acid through a Friedel-Crafts alkylation with an acid such as sulfuric acid and the desired hydroxymethyl amide. The resulting product, compound (3), can then be coupled with a suitable 2-aminoimidazole under typical coupling conditions as described in Scheme A, Step 1, to give compounds of Formula I.

Scheme B

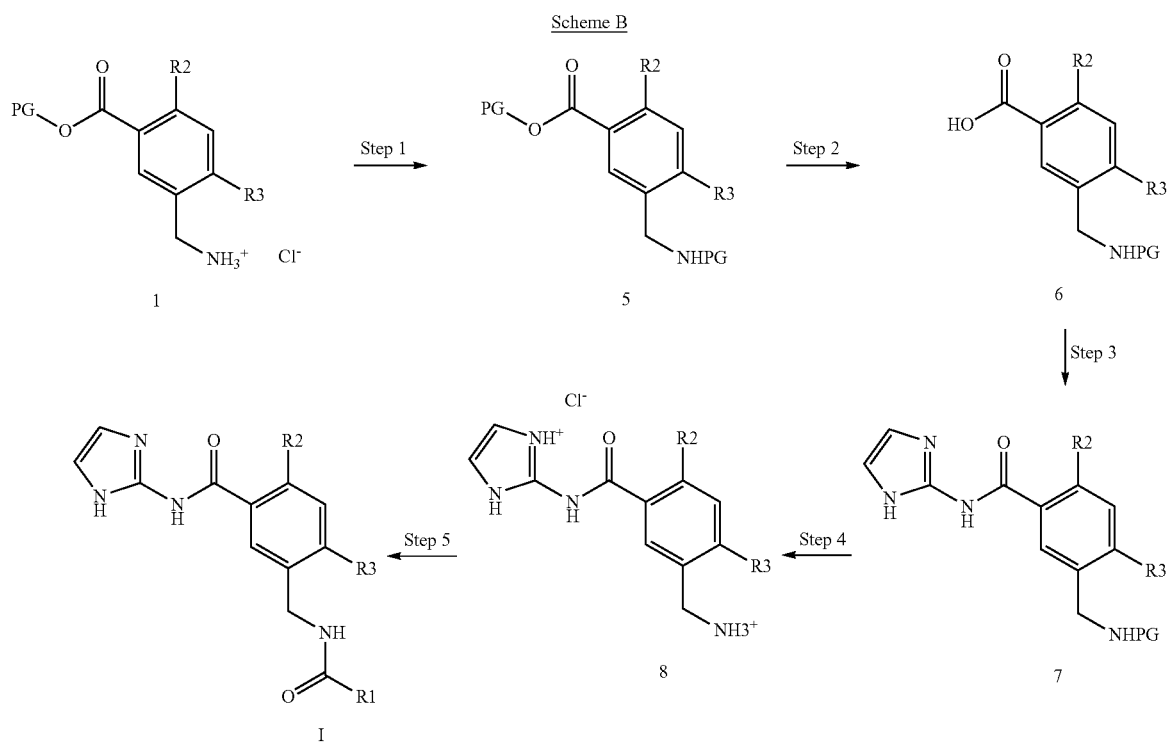

Scheme B illustrates the preparation of compounds of Formula I by configuring the imidazole at the benzoic acid position and then acylating the benzyl amine to form compounds of Formula I.

In Step 1 of Scheme B, compound 1, the benzyl amine of the substituted protected benzoic acid is protected with a protecting group such as t-butoxycarbonyl using an organic base such as triethylamine to give compound 5. The protected benzoic acid is then deprotected with an aqueous base such as sodium hydroxide or lithium hydroxide to give compound 6, which is then coupled with 2-aminoimidazole to give compound 7. Coupling conditions are described in Scheme 1, Step 3. The amine protecting group can then be removed under acidic conditions such as hydrochloric acid to give compound 8 (Step 4). The amine group on compound 8 can then be coupled with appropriate carboxylic acids or acid chlorides as described in Scheme A, Step 1 to give compounds of Formula I.

PREPARATIONS AND EXAMPLES

Unless noted to the contrary, the compounds illustrated herein are named and numbered using Symyx® Draw version 3.2 (Symyx Solutions, Inc.) or IUPACNAME ACDLABS.

Preparation 1

3-Bromo-4-(dibromomethyl)benzonitrile

Heat a mixture of 3-bromo-4-methylbenzonitrile (25.0 g, 127.5 mmol, 1.0 equiv) and NBS (5.53 g, 306.1 mmol, 2.4 equiv) in carbon tetrachloride (200 mL) to 95° C. for two days. Cool the resulting suspension and remove the solids by filtration. Concentrate the filtrate under reduced pressure, and subject the resulting crude material to chromatography on silica gel eluting with a 2-5% THF/hexanes gradient to give the title compound (37.09 g, 82%). $^1$H NMR (CDCl$_3$, 400 MHz): δ 8.10 (d, 1H, J=8.2 Hz), 7.79 (d, 1H, J=1.3 Hz), 7.67 (dd, 1H, J=8.2, 1.3 Hz), 6.99 (s, 1H).

Preparation 2

3-Bromo-4-(difluoromethyl)benzonitrile

To a solution of 3-bromo-4-(dibromomethyl)benzonitrile (19.2 g, 54.3 mmol, 1.0 equiv) in dichloromethane (200 mL) under a nitrogen atmosphere, add silver tetrafluoroborate (26.69 g, 135.7 mmol, 2.5 equiv) and stir overnight at room temperature. Remove the solids by filtration, concentrate the filtrate under reduced pressure, and subject the resulting crude material to chromatography on silica gel eluting with a 2-5% THF/hexanes gradient to give the title compound (9.0 g, 71%). GS/MS (m/z) ($^{79}$Br/$^{81}$Br) 231/233 (M).

Preparation 3

Methyl 5-cyano-2-(difluoromethyl)benzoate

Purge a mixture of 3-bromo-4-(difluoromethyl)benzonitrile (8.87 g, 38.2 mmol, 1.0 equiv), triethylamine (16.0 mL, 114.7 mmol, 3.0 equiv), methanol (70 mL), and DMF (120 mL) with nitrogen, then treat the mixture with palladium(II) acetate (867 mg, 3.82 mmol, 0.1 equiv) and 1,3-bis(diphenylphosphino)propane (1.61 g, 3.82 mmol, 0.1 equiv). Stir the mixture under 138 kPaG of carbon monoxide at room temperature for two days and then 80° C. for one day. Cool the mixture to room temperature and dilute with Et$_2$O (300 mL). Wash the mixture with water and saturated aqueous NaCl, and separate the organic layer. Dry the organic layer over sodium sulfate, filter, and concentrate under reduced pressure. Subject the resulting crude material to chromatography on silica gel eluting with a 10-15% THF/hexanes gradient to give the title compound (6.19 g, 77%). GC/MS (m/z) 211 (M).

Preparation 4

Benzyl 5-cyano-2-(trifluoromethyl)benzoate

Under a nitrogen atmosphere, to a solution of 5-chloro-2-(trifluoromethyl)benzoic acid (5.02 g, 22.35 mmol, 1.0 equiv) in DMA (45 mL), add zinc(II) cyanide (1.77 g, 15.07 mmol, 0.67 equiv), zinc dust (<10 μM, 330 mg, 5.05 mmol, 0.23 equiv), and bis(tri-tert-butylphosphino)palladium (540 mg, 1.06 mmol, 0.05 equiv). Stir the mixture under a nitrogen atmosphere at 95° C. for 9.5 hours. Add cesium carbonate (13.3 g, 40.82 mmol, 1.83 equiv), then benzyl bromide (3.0 mL, 25.15 mmol, 1.13 equiv), and stir under air at room temperature for 3.5 hours. Concentrate under reduced pressure, add water, and extract with EtOAc. Separate the organic phase and wash with saturated aqueous NaCl, dry over MgSO$_4$, filter, and concentrate under reduced pressure. Subject the resulting crude material to flash chromatography on silica gel eluting with a 0-50% EtOAc/hexanes gradient to give the title compound (3.9 g, 57%). MS (m/z) 306 (M+1).

Preparation 5

5-(Aminomethyl)-2-(trifluoromethyl)benzoic acid

Combine benzyl 5-cyano-2-(trifluoromethyl)benzoate (3.9 g, 12.78 mmol, 1.0 equiv), palladium (10 wt % on carbon, 400 mg, 0.38 mmol, 0.03 equiv), and methanol (128 mL), and purge the mixture with hydrogen. Stir overnight under a hydrogen atmosphere. Filter the mixture through a pad of diatomaceous earth, and then rinse the pad with hot methanol (3×150 mL) to bring through precipitated product. Concentrate the filtrate under reduced pressure to give the title compound (1.4 g, 50%). MS (m/z) 220 (M+1).

Preparation 6

N-(Hydroxymethyl)-2,2-dimethylpropanamide

To a mixture of 2,2-dimethylpropanamide (5.0 g, 49.4 mmol, 1.0 equiv) and aqueous sodium hydroxide (1 M, 0.494 mL, 0.494 mmol, 0.01 equiv), add aqueous formaldehyde (13.31 M, 3.71 mL, 49.4 mmol, 1.0 equiv). Stir at room temperature for 2 h, and concentrate under reduced pressure to give a white solid. Dilute the crude material with dichloromethane, dry over MgSO$_4$, filter, and concentrate under reduced pressure to give the title compound as a white solid (6.4 g, 99%). $^1$H NMR (DMSO-d$_6$, 400 MHz): δ 8.14 (br s, 1H), 5.40 (t, 1H, J=6.7 Hz), 4.46 (app t, 2H, J=6.6 Hz), 1.06 (s, 9H).

Preparation 7

N-(Hydroxymethyl)-2-methylpropanamide

Prepare essentially by the method of Preparation 6 using the appropriate amide. $^1$H NMR (CDCl$_3$, 400 MHz) 6.51 (br s, 1H), 4.72 (dd, 2H, J=7.5, 6.8 Hz), 3.63 (t, 1H, J=7.7 Hz), 2.35 (sep, 1H, J=6.9 Hz), 1.13 (d, 6H, J=6.9 Hz).

Preparation 8

5-[(2,2-Dimethylpropanoylamino)methyl]-2-methylbenzoic acid

Cool sulfuric acid (3.67 mL) to 0° C., and add 2-methylbenzoic acid (500 mg, 3.67 mmol, 1.0 equiv) and N-(hydroxymethyl)-2,2-dimethylpropanamide (506 mg, 3.86 mmol, 1.05 equiv). Allow the mixture to warm to room temperature, and stir overnight. Dilute with water (25 mL) and extract with EtOAc (50 mL). Dry the organic layer over MgSO$_4$, filter, and concentrate under reduced pressure to give the crude compound. Purify the material by reverse-phase HPLC on an XBridge Prep C18 5 μM OBD 30×75 mm column, eluting with a gradient of 5-50% (0.1% TFA in acetonitrile) in (0.1% TFA in water) to give the title compound (255 mg, 28%). $^1$H NMR (DMSO-d$_6$, 400 MHz): δ 12.76 (s, 1H), 8.09 (t, 1H, J=6.0 Hz), 7.67 (d, 1H, J=1.6 Hz), 7.25 (dd, 1H, J=8.0, 1.6 Hz), 7.21 (d, 1H, J=8.0 Hz), 4.22 (d, 2H, J=6.0 Hz), 2.46 (s, 3H), 1.10 (s, 9H).

Prepare the following compounds in Table 1 essentially by the method of Preparation 11 with the appropriate benzoic acid and N-hydroxymethyl amide.

TABLE 1

| Prep. No. | Chemical Name | $^1$H NMR (DMSO-d$_6$, 400 MHz) |
|---|---|---|
| 9 | 2-Bromo-5-[(2,2-dimethylpropanoylamino)methyl]benzoic acid | 8.15 (t, 1H, J = 6.2 Hz), 7.63 (d, 1H, J = 8.3 Hz), 7.57 (d, 1H, J = 2.5 Hz), 7.24 (dd, 1H, J = 8.3, 2.3 Hz), 4.21 (d, 2H, J = 6.0 Hz), 1.10 (s, 9H). |
| 10 | 2-Chloro-4-fluoro-5-[(2-methylpropanoylamino)methyl]benzoic acid | 13.44 (s, 1H), 8.35 (t, 1H, J = 6.3 Hz), 7.76 (d, 1H, J = 8.3 Hz), 7.51 (d, 1H, J = 9.9 Hz), 4.25 (d, 2H, J = 5.8 Hz), 2.41 (sep, 1H, J = 6.9 Hz), 1.00 (d, 6H, J = 6.8 Hz) |
| 11 | 2-Chloro-4-methyl-5-[(2-methylpropanoylamino)methyl]benzoic acid | 13.19 (s, 1H), 8.24 (t, 1H, J = 6.0 Hz), 7.61 (s, 1H), 7.35 (s, 1H), 4.19 (d, 2H, J = 5.9 Hz), 2.42 (sep, 1H, J = 6.8 Hz), 1.01 (d, 6H, J = 7.0 Hz) |

Preparation 12

Methyl 5-(aminomethyl)-2-(difluoromethyl)benzoate hydrochloride

Purge a mixture of methyl 5-cyano-2-(difluoromethyl)benzoate (9.37 g, 44.4 mmol, 1.0 equiv), palladium (10% on carbon, 3.00 g, 2.82 mmol, 0.064 equiv), and methanol (50 mL) with nitrogen, then add hydrochloric acid (37 wt % aqueous, 8.0 mL, 105.6 mmol, 2.38 equiv), and stir the resulting suspension under 275 kPaG of hydrogen at room temperature overnight. Remove the solids by filtration, concentrate the filtrate under reduced pressure, and dry the resulting material in a 40° C. vacuum oven overnight to give the title compound as a light brown solid (7.01 g, 83%). MS (m/z) 216 (M+1).

Preparation 13

Methyl 5-(tert-butoxycarbonylaminomethyl)-2-(difluoromethyl)benzoate

To a solution of methyl 5-(aminomethyl)-2-(difluoromethyl)benzoate hydrochloride (1.76 g, 6.99 mmol, 1.0 equiv) in methanol (30 mL), add triethylamine (2.14 mL, 15.39 mmol, 2.2 equiv) and di-tert-butyldicarbonate (1.89 g, 8.39 mmol, 1.2 equiv). Stir the mixture for 30 min at room temperature and concentrate under reduced pressure. Dilute with EtOAc (100 mL), and wash with water and saturated aqueous NaCl. Separate the organic layer and dry over Na$_2$SO$_4$, filter, and concentrate under reduced pressure. Subject the crude material to flash chromatography on silica gel eluting with a 5-10% THF/hexanes gradient to give the title compound (2.0 g, 90%). MS (m/z) 314 (M−1).

Prepare the following compound essentially by the method of Preparation 13 with the appropriate ammonium salt or primary amine

TABLE 2

| Prep. No. | Chemical Name | MS (m/z) | Comment |
|---|---|---|---|
| 15 | 5-(tert-Butoxycarbonylaminomethyl)-2-(trifluoromethyl)benzoic acid | 337 (M + 18) | a | a The product is not subjected to chromatography.

Preparation 16

2-(Difluoromethyl)-5-[(2-methylpropanoylamino)methyl]benzoic acid

To a mixture of methyl 5-(aminomethyl)-2-(difluoromethyl)benzoate hydrochloride (1.30 g, 5.17 mmol, 1.0 equiv) and triethylamine (1.51 mL, 10.85 mmol, 2.1 equiv) in dichloromethane (50 mL) at room temperature, add isobutyryl chloride (0.571 mL, 5.42 mmol, 1.05 equiv) and stir for one hour. Dilute the mixture with dichloromethane and wash with water then saturated aqueous NaCl. Separate the organic layer and dry over sodium sulfate, filter, and concentrate under reduced pressure. Dissolve the resulting crude material in 1,4-dioxane (10 mL), and add sodium hydroxide (5 N aqueous, 2 mL, 10 mmol, 1.93 equiv). Stir the resulting suspension at 40° C. overnight. Concentrate the mixture under reduced pressure, and treat the resulting residue with 1 N aqueous hydrochloric acid until the pH reaches 3. Extract the resulting suspension with EtOAc (2×30 mL). Wash the combined organic layers with saturated aqueous NaCl (50 mL), dry over sodium sulfate, filter, and concentrate under reduced pressure to give the title compound as a white solid (1.32 g, 94%). MS (m/z) 272 (M+1).

Preparation 17

5-(tert-Butoxycarbonylaminomethyl)-2-(difluoromethyl)benzoic acid

Treat a solution of methyl 5-(tert-butoxycarbonylaminomethyl)-2-(difluoromethyl)benzoate (1.43 g, 4.54 mmol, 1.0 equiv) in 1,4-dioxane (20 mL) with sodium hydroxide (5 N aqueous, 1.81 mL, 9.07 mmol, 2.0 equiv), and stir the mixture at room temperature overnight. Concentrate under reduced pressure, and adjust the pH to 4 with aqueous HCl. Extract with EtOAc (2×40 mL), and wash the combined organic extracts with saturated aqueous NaCl, separate, and dry the organic phase over $Na_2SO_4$, filter, and concentrate under reduced pressure to give the title compound (1.21 g, 88%). MS (m/z) 319 (M+18).

Preparation 18

5-[(tert-Butoxycarbonylaminomethyl)-2-chloro-N-(1H-imidazol-2-yl)benzamide

To a mixture of 2-aminoimidazole monosulfate (1.29 g, 7.0 mmol, 1.0 equiv) and 5-[(tert-butoxycarbonylamino)methyl]-2-chlorobenzoic acid (2.00 g, 7.0 mmol, 1.0 equiv), add DMF (14.0 mL), DIEA (5.13 mL, 29.4 mmol, 4.2 equiv) and BOP (3.83 g, 8.4 mmol, 1.2 equiv). Stir at 60° C. for 5 h. Isolate the resulting white precipitate by filtration. Triturate the solids with 10% MeOH/dichloromethane (800 mL), and filter the mixture through a pad of silica gel. Concentrate the filtrate under reduced pressure, triturate the resulting solid with $Et_2O$ (10 mL), and isolate the title compound by filtration as a white solid (1.01 g, 41%). MS (m/z) ($^{35}Cl/^{37}Cl$) 351/353 (M+1).

Prepare the following compounds essentially by the method of Preparation 18 with the appropriate benzoic acids.

TABLE 3

| Prep. No. | Chemical Name | MS (m/z) | Comment |
|---|---|---|---|
| 19 | 5-(tert-Butoxycarbonylaminomethyl)-2-(difluoromethyl)-N-(1H-imidazol-2-yl)benzamide | 367 (M + 1) | a |
| 20 | 5-(tert-Butoxycarbonylaminomethyl)-2-(trifluoromethyl)-N-(1H-imidazol-2-yl)benzamide | 385 (M + 1) | b | a The reaction mixture is heated to 60° C. overnight, diluted with EtOAc, washed with 1N NaOH, water, and brine, and the title compound is collected by filtration.
b The reaction mixture is heated to 60° C. overnight, cooled to room temperature, quenched with saturated aqueous LiCl, extracted with EtOAc, washed with saturated aqueous NaCl, dried over $MgSO_4$, filtered, concentrated under reduced pressure, then dissolved in a minimal volume of EtOAc and allowed to stand until the product, which was thereafter isolated by filtration, precipitated out.

Preparation 21

5-(Aminomethyl)-2-chloro-N-(1H-imidazol-2-yl)benzamide dihydrochloride

Dissolve 5-[(tert-butoxycarbonylaminomethyl)-2-chloro-N-(1H-imidazol-2-yl)benzamide (640 mg, 1.82 mmol, 1.0 equiv) in hydrochloric acid (4 M in dioxane, 4.56 mL, 18.24 mmol, 10.0 equiv) and stir at room temperature for 1 h. Pour the reaction mixture into vigorously swirling EtOAc (50 mL), isolate the resulting white precipitate by filtration, wash with EtOAc (25 mL), and dry in a 40° C. vacuum oven overnight to provide the title compound as a white solid (590 mg, 100%). $^1$H NMR ($D_2O$, 400 MHz) δ 7.53 (d, 1H, J=2.0 Hz), 7.48 (d, 1H, J=8.3 Hz), 7.46 (dd, 1H, J=8.3, 2.0 Hz), 7.04 (s, 2H), 4.05 (s, 2H).

Prepare the following compounds essentially by the method of Preparation 21 using the appropriate tert-butyl carbamates.

TABLE 4

| Prep. No. | Chemical Name | $^1$H NMR (400 MHz) | Comment |
|---|---|---|---|
| 22 | 5-(Aminomethyl)-N-(1H-imidazol-2-yl)-2-(trifluoromethyl)benzamide dihydrochloride | 8.66 (br s, 3H), 7.93 (d, 1H, J = 8.4 Hz), 7.92 (s, 1H), 7.85 (d, 1H, J = 8.4 Hz), 7.09 (br s, 2H), 4.15 (br q, 2H, J = 5.6 Hz) | a |
| 23 | 5-(Aminomethyl)-N-(1H-imidazol-2-yl)-2-(difluoromethyl)benzamide dihydrochloride | 7.77 (d, 1H, J = 7.9 Hz) 7.69 (s, 1H), 7.68 (d, 1H, J = 7.9 Hz), 7.08 (s, 2H), 7.03 (t, 1H, J = 55 Hz), 4.17 (s, 2H) | b | a The NMR spectrum is obtained in DMSO-$d_6$.
b The NMR spectrum is obtained in $D_2O$.

Preparation 24

Methyl 2-chloro-5-[(2,2-dimethylpropanoylamino)methyl]benzoate

To a thermally controlled reactor, add methyl 5-(aminomethyl)-2-chlorobenzoate hydrochloride (700 g, 3.51 mol, 1.0 equiv), dichloromethane (4.9 L), and N,N-diisopropylethylamine (1.71 L, 9.82 mol, 2.8 equiv). Add pivaloyl chloride (515 mL, 4.21 mol, 1.2 equiv) dropwise at such a rate that the internal temperature does not exceed 21° C. Upon completion of the addition, stir the reaction mixture at room temperature for one hour. Quench the reaction mixture with saturated aqueous sodium bicarbonate (10 L). Extract the mixture with dichloromethane (2×1 L), combine the organic extracts, dry over sodium sulfate, filter, and concentrate under reduced pressure to give an oil, (1.1 kg) carried on crude without further purification. MS (m/z) ($^{35}Cl/^{37}Cl$) 284/286 (M+1)

Preparation 25

2-Chloro-5-[(2,2-dimethylpropanoylamino)methyl]benzoic acid

Add methyl 2-chloro-5-[(2,2-dimethylpropanoylamino)methyl]benzoate (1.05 kg, 3.7 mol), 1,4-dioxane (5.25 L) and water (3.15 L) together and then add lithium hydroxide (407.8 g, 9.6 mol). Stir the resulting suspension at room temperature for one hour. Acidify the mixture to pH 1 with 5 N aqueous HCl in a dropwise fashion at a rate such that the internal temperature does not exceed 30° C. Concentrate the solution to remove approximately 6 L of solvent, and cool the resulting suspension to 10° C. Filter, wash the resulting solid material with water (8 L), and allow to dry on the sinter for 3 h. Collect the solid, and dry the material in a vacuum oven at 40° C. for 48 h to give the title compound as a free-flowing white solid (775 g, 77.7%). MS (m/z) ($^{35}Cl/^{37}Cl$) 270/272 (M+1).

Example 1

2-Chloro-N-(1H-imidazol-2-yl)-4-methyl-5-[(2-methylpropanoylamino)methyl]benzamide

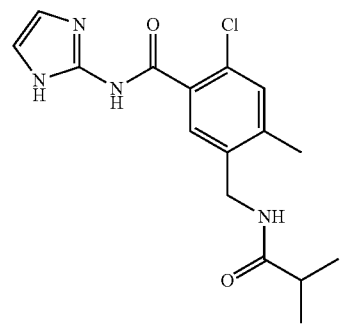

To a mixture of 2-chloro-4-methyl-5-[(2-methylpropanoylamino)methyl]benzoic acid (75.0 mg, 0.28 mmol, 1.0 equiv) and 2-aminoimidazole monosulfate (51.4 mg, 0.28 mmol, 1.0 equiv) in DMF (0.56 mL), add DIEA (0.204 mL, 1.17 mmol, 4.2 equiv) and BOP (152 mg, 0.33 mmol, 1.2 equiv). Stir at 60° C. for 5 h and isolate the resulting precipitate by filtration. Triturate with 9:1 dichloromethane:methanol (800 mL), and filter through a pad of silica gel. Concentrate the filtrate under reduced pressure to furnish the title compound as a white solid (57 mg, 61% yield): $^1$H NMR (DMSO-$d_6$, 400 MHz): δ 11.76 (br s, 2H), 8.20 (t, 1H, J=6.0 Hz), 7.33 and 7.33 (s and s, 1H and 1H, isochronous), 6.75 (br s, 2H), 4.21 (d, 2H, J=5.7 Hz), 2.42 (sep, 1H, J=6.8 Hz), 2.28 (s, 3H), 1.00 (d, 6H, J=6.8 Hz). MS (m/z) ($^{35}Cl/^{37}Cl$) 335/337 (M+1).

Prepare the following compounds essentially by the method of Example 1 with the appropriate benzoic acids.

TABLE 5

| Ex. No. | Chemical Name | Structure | MS (m/z) | Condition |
|---|---|---|---|---|
| 2 | 5-[(2,2-Dimethylpropanoylamino)methyl]-N-(1H-imidazol-2-yl)-2-methyl-benzamide | 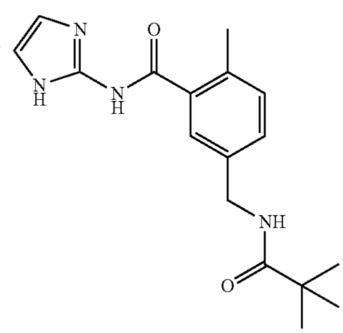 | 315 (M + 1) | a |

TABLE 5-continued

| Ex. No. | Chemical Name | Structure | MS (m/z) | Condition |
|---|---|---|---|---|
| 3 | 2-(Difluoromethyl)-N-(1H-imidazol-2-yl)-5-[(2-methylpropanoylamino)methyl]benzamide | 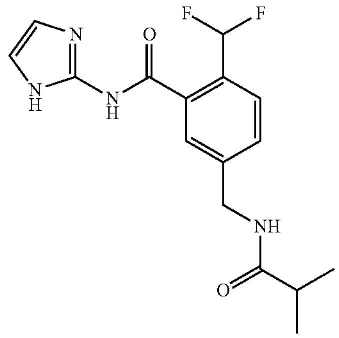 | 337 (M + 1) | b |
| 4 | 2-Chloro-4-fluoro-N-(1H-imidazol-2-yl)-5-[(2-methylpropanoylamino)methyl]benzamide | 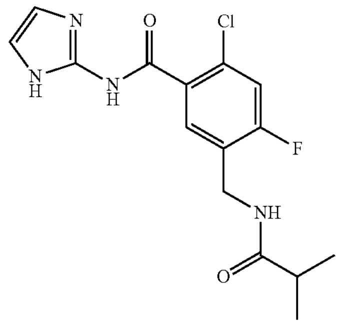 | 339/341 (M + 1) | c |
| 5 | 2-Bromo-5-[(2,2-dimethylpropanoylamino)methyl]-N-(1H-imidazol-2-yl)benzamide | | 379/381 (M + 1) | d | a: The mixture is heated to 60° C. overnight, the product precipitates from the reaction mixture, is isolated by filtration, and rinsed with EtOAc.
b: The reaction mixture is heated to 60° C. overnight, diluted with EtOAc, washed with 1 N NaOH, water, saturated aqueous NaCl, dried over $Na_2SO_4$, concentrated, and recrystallized from EtOAc/methanol.
c: The reaction mixture is heated to 60° C. overnight, purified twice with reverse-phase chromatography on a C18 column eluting with a gradient of 10-60% (0.1% TFA/acetonitrile) to (0.1% TFA/water). The purified material is partitioned between EtOAc and saturated aqueous $NaHCO_3$, dried over $Na_2SO_4$, filtered, and concentrated under reduced pressure to give the title compound.
d: The reaction mixture is heated to 60° C. overnight, diluted with EtOAc and saturated aqueous LiCl, the organic layer is washed with saturated aqueous NaCl, dried over $MgSO_4$, filtered, and concentrated under reduced pressure. The crude material is purified by reverse-phase HPLC on an XBridge Prep C18 5 μM OBD 30 × 75 mm column, eluting with a gradient of 5-50% (0.1% TFA in acetonitrile) in (0.1% TFA in water).

H NMR (DMSO-$d_6$, 400 MHz)

Ex 2: 11.72 (br s, 2H), 8.05 (t, 1H, J=5.9 Hz), 7.32 (s, 1H), 7.20 and 7.20 (s and s, 1H and 1H, isochronous), 6.72 (br s, 2H), 4.23 (d, 2H, J=6.2 Hz), 2.34 (s, 3H), 1.10 (s, 9H).

Ex 3: 11.88 (br s, 2H), 8.29 (t, 1H, J=5.6 Hz), 7.71 (br s, 1H), 7.62 (d, 1H, J=8.0 Hz), 7.56 (br t, 1H, J=58 Hz), 7.40 (dd, 1H, J=8.0, 0.8 Hz), 6.78 (s, 2H), 4.28 (d, 2H, J=5.8 Hz), 2.39 (sep, 1H, J=6.8 Hz), 0.99 (d, 6H, J=6.9 Hz).

Ex 4: 11.81 (br s, 2H), 8.32 (t, 1H, J=5.6 Hz), 7.49 (d, 1H, J=10.0 Hz), 7.47 (d, 1H, J=7.9 Hz), 6.77 (s, 2H), 4.27 (d, 2H, J=6.0 Hz), 2.40 (sep, 1H, J=6.8 Hz), 0.99 (d, 6H, J=6.8 Hz).

Ex 5: 11.77 (s, 2H), 8.14 (t, 1H, J=6.2 Hz), 7.59 (d, 1H, J=8.3 Hz), 7.34 (d, 1H, J=2.1 Hz), 7.20 (dd, 1H, J=8.0, 2.1 Hz), 6.75 (br s, 2H), 4.23 (d, 2H, J=6.0 Hz), 1.10 (s, 9H).

Example 6

2-Chloro-N-(1H-imidazol-2-yl)-5-[[(1-methylcyclopropanecarbonyl)amino]methyl]benzamide

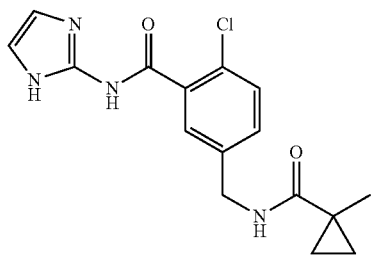

Dissolve 5-(aminomethyl)-2-chloro-N-(1H-imidazol-2-yl)benzamide dihydrochloride (100 mg, 0.35 mmol, 1.0 equiv) and 1-methylcyclopropanecarboxylic acid (45.3 mg, 0.45 mmol, 1.3 equiv) in DMF (0.697 mL), add triethylamine (82.5 μL, 0.59 mmol, 1.7 equiv) and BOP (231 mg, 0.52 mmol, 1.5 equiv). Stir the mixture at 60° C. overnight, and purify the crude mixture by flash chromatography on silica gel eluting with a 20% to 60% EtOAc/hexanes gradient. Recrystallize the material from EtOAc, filter, and wash with EtOAc to provide the title compound as a white solid (116 mg, 55%). $^1$H NMR (DMSO-$d_6$, 400 MHz) δ 11.76 (br s, 2H), 8.13 (t, 1H, J=6.0 Hz), 7.43 (d, 1H, J=8.2 Hz), 7.39 (d, 1H, J=1.3 Hz), 7.29 (dd, 1H, J=8.2, 1.3 Hz), 6.74 (br s, 2H), 4.25 (d, 2H, J=6.0 Hz), 1.26 (s, 3H), 0.93 (app q, 2H, J=3.1 Hz), 0.50 (app q, 2H, J=3.2 Hz). MS (m/z) ($^{35}$Cl/$^{37}$Cl) 333/335 (M+1).

Prepare the following compounds essentially by the method of Example 6 with the appropriate ammonium salts and carboxylic acids.

TABLE 6

| Ex. No | Chemical Name | Structure | MS (m/z) | |
|---|---|---|---|---|
| 7 | 2-Chloro-N-(1H-imidazol-2-yl)-5-[[(2-methoxy-2-methyl-propanoyl)amino]methyl]benzamide | 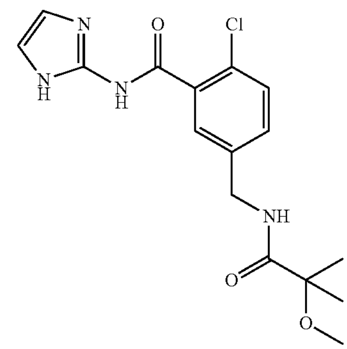 | ($^{35}$Cl/$^{37}$Cl) 351/353 (M + 1) | a |
| 8 | 2-(Difluoromethyl)-N-(1H-imidazol-2-yl)-5-[[[(2S)-2-methylbutanoyl]amino]methyl]benzamide | Chiral | 351 (M + 1) | b | a: Purification is reverse-phase HPLC on an XBridge Prep C18 5 μM OBD 30 × 75 mm column, eluting with a gradient of 5-50% (0.1% TFA in acetonitrile) in (0.1% TFA in water).

b The crude reaction mixture is concentrated and subjected to reverse-phase chromatography on a C18 column, eluting with TFA/acetonitrile/water.

¹H NMR (DMSO-d₆, 400 MHz)

Ex 7: 11.62 (br s, 2H), 8.39 (t, 1H, J=6.1 Hz), 7.43 (d, 1H, J=8.2 Hz), 7.40 (d, 1H, J=2.1 Hz), 7.30 (dd, 1H, J=8.2, 2.1 Hz), 6.73 (s, 2H), 4.25 (d, 2H, J=6.3 Hz), 3.13 (s, 3H), 1.24 (s, 6H).

Ex 8: 11.95 (br s, 2H), 8.36 (t, 1H, J=5.6 Hz), 7.76 (br s, 1H), 7.66 (d, 1H, J=8.0 Hz), 7.59 (br t, 1H, J=55 Hz), 7.45 (d, 1H, J=8.0 Hz), 6.80 (s, 2H), 4.33 (d, 2H, J=5.6 Hz), 2.22 (app sextet, 1H, J=7.2 Hz), 1.53 (ddq, 1H, J=13.6, 7.6, 7.6 Hz), 1.32 (ddq, 1H, J=13.6, 6.4, 6.4 Hz), 1.01 (d, 3H, J=6.4 Hz), 0.80 (app t, 3H, J=7.4 Hz).

Example 9

2-Chloro-N-(1H-imidazol-2-yl)-5-[[[1-(trifluoromethyl)cyclopropanecarbonyl]amino]methyl]benzamide

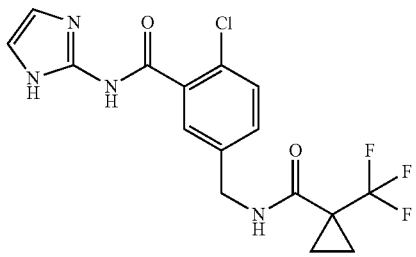

To a suspension of 1-(trifluoromethyl)cyclopropanecarboxylic acid (54 mg, 0.34 mmol, 1.1 equiv) and 5-(aminomethyl)-2-chloro-N-(1H-imidazol-2-yl)benzamide dihydrochloride (100 mg, 0.31 mmol, 1.0 equiv) in THF (1.55 mL), add DIEA (0.189 mL, 1.08 mmol, 3.5 equiv), HOBt (59.2 mg, 0.386 mmol, 1.08 equiv), EDCI (74 mg, 0.386 mmol, 1.08 equiv), and stir the reaction mixture at room temperature for three days. Concentrate under reduced pressure, and subject the crude mixture to chromatography on a C18 reversed-phase stationary phase eluting with a 5-60% (0.1% TFA in acetonitrile) in (0.1% TFA in water) gradient to give the title compound as a white solid (39 mg, 33%). ¹H NMR (DMSO-d₆, 400 MHz): δ 11.80 (br s, 2H), 8.41 (t, 1H, J=5.8 Hz), 7.46 (d, 1H, J=8.3 Hz), 7.40 (d, 1H, J=2.1 Hz), 7.30 (dd, 1H, J=8.3, 2.1 Hz), 6.75 (br s, 2H), 4.28 (d, 2H, J=6.0 Hz), 1.33-1.20 (m, 4H). MS (m/z) ($^{35}$Cl/$^{37}$Cl) 387/389 (M+1).

Example 10

2-Chloro-5-[(2-methylpropanoylamino)methyl]-N-(1H-imidazol-2-yl)benzamide

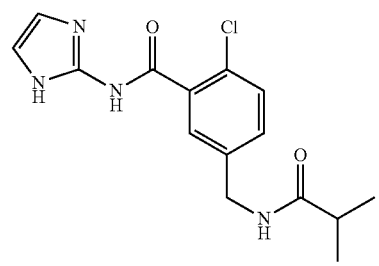

To a suspension of 5-(aminomethyl)-2-chloro-N-(1H-imidazol-2-yl)benzamide dihydrochloride (50 mg, 0.154 mmol, 1.0 equiv) in THF (0.77 mL), add triethylamine (80 μL, 0.57 mmol, 3.7 equiv) and isobutyryl chloride (16.3 μL, 0.154 mmol, 1.0 equiv), and stir the reaction mixture for 1 h at room temperature. Concentrate the reaction mixture under reduced pressure, triturate the crude solids with a mixture of water (10 mL), hexanes (10 mL), and diethyl ether (10 mL), isolate the white solid by filtration and dry in a 40° C. vacuum oven to give the title compound (19 mg, 38% yield): ¹H NMR (DMSO-d₆, 400 MHz): δ 11.74 (br s, 2H), 8.30 (t, 1H, J=6.0 Hz), 7.42 (d, 1H, J=8.0 Hz), 7.36 (d, 1H, J=2.0 Hz), 7.26 (dd, 1H, J=8.0, 2.0 Hz), 6.73 (br s, 2H), 4.22 (d, 2H, J=5.9 Hz), 2.37 (septet, 1H, J=6.6 Hz), 0.97 (d, 6H, J=6.8 Hz). MS (m/z) ($^{35}$Cl/$^{37}$Cl) 321/323 (M+1).

Prepare the following compounds essentially by the method of Example 10 with the appropriate ammonium salts and acid chlorides.

TABLE 7

| Ex. No | Chemical Name | Structure | MS (m/z) | |
|---|---|---|---|---|
| 11 | 2-(Difluoromethyl)-5-[(2,2-dimethylpropanoylamino)methyl]-N-(1H-imidazol-2-yl)benzamide | 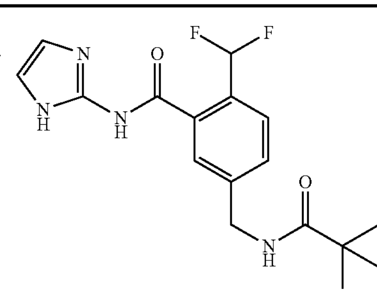 | 351 (M + 1) | a |

TABLE 7-continued

| Ex. No | Chemical Name | Structure | MS (m/z) | |
|---|---|---|---|---|
| 12 | 2-(Trifluoromethyl)-5-[(2,2-dimethylpropanoylamino)methyl]-N-(1H-imidazol-2-yl)benzamide | 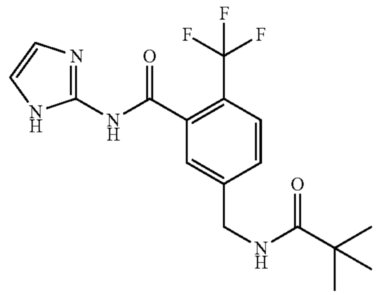 | 369 (M + 1) | b |
| 13 | 2-Chloro-5-[(2,2-dimethylbutanoylamino)methyl]-N-(1H-imidazol-2-yl)benzamide | | ($^{35}$Cl/$^{37}$Cl) 349/351 (M + 1) | c | a: The reaction mixture is concentrated under reduced pressure and subjected to chromatography on silica gel, eluting with a 5-10% methanol/dichloromethane gradient. The purified material is triturated with Et$_2$O to provide the title compound.
b: The reaction mixture is concentrated under reduced pressure and subjected to chromatography on silica gel, eluting with a 0-100% EtOAc/hexanes gradient.
c: The reaction mixture is concentrated under reduced pressure and subjected to reverse-phase chromatography on a C18 column eluting with a gradient of 5-60% (0.1% TFA/acetonitrile) in (0.1% TFA/water).

$^1$H NMR (DMSO-d$_6$, 400 MHz)
Ex 11: 11.88 (br s, 2H), 8.11 (t, 1H, J=6.0 Hz), 7.70 (br s, 1H), 7.61 (d, 1H, J=8.0 Hz), 7.57 (br t, 1H, J=55 Hz), 7.38 (d, 1H, J=8.0 Hz), 6.78 (s, 2H), 4.28 (d, 2H, J=5.8 Hz), 1.09 (s, 9H)
Ex 12: 11.84 (s, 2H), 8.20 (t, 1H, J=6.2 Hz), 7.74 (d, 1H, J=8.1 Hz), 7.48 (s, 1H), 7.45 (d, 1H, J=8.2 Hz), 6.75 (s, 2H), 4.33 (d, 2H, J=6.0 Hz), 1.12 (s, 9H)
Ex 13: 14.12 (br s, 2H), 7.63 (br s, 1H), 7.42 and 7.42 (isochronous br s and s, 1H and 1H), 7.01 (s, 2H), 6.43 (t, 1H, J=5.6 Hz), 4.48 (d, 2H, J=5.5 Hz), 1.55 (q, 2H, J=7.4 Hz), 1.16 (s, 6H), 0.81 (t, 3H, J=7.3 Hz)

Example 14

2-Chloro-5-[(2,2-dimethylpropanoylamino)methyl]-N-(1H-imidazol-2-yl)benzamide

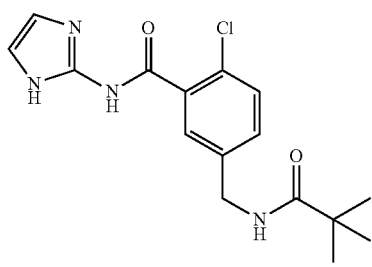

To a thermally controlled reaction vessel, add 2-chloro-5-[(2,2-dimethylpropanoylamino)methyl]benzoic acid (420 g, 1.56 mol, 1.0 equiv), 2-aminoimidazole monosulfate (349 g, 1.87 mol, 1.2 equiv), N,N-dimethylformamide (2.94 L), O-benzotriazol-1-yl-N,N,N',N'-tetramethyluronium tetrafluoroborate (722 g, 2.18 mol, 1.4 equiv), and N,N-diisopropylethylamine (869 mL, 4.98 mol, 3.2 equiv). Heat the resulting suspension to an internal temperature of 80° C. for 18 hours. Cool the reaction mixture to 10° C., pour the mixture into ice water (14 L), and stir for 90 min. Collect the solids by filtration, dry the material in air for 24 h, and in a vacuum oven at 50° C. for 24 h. Slurry the solid material in isopropanol (7 L), heat to an internal temperature of 73° C. for 3 h, and cool to 10° C. Filter the suspension to isolate the solid material. Dry the material in air for 24 h and in a vacuum oven at 55° C. for 48 h to give the title compound as an off-white solid (435 g, 83.4%). $^1$H NMR (DMSO-d$_6$, 400 MHz): δ 11.84 (s, 2H), 8.13 (t, 1H, J=6.0 Hz), 7.47 (d, 1H, J=8.3 Hz), 7.40 (d, 1H, J=1.7 Hz), 7.31 (dd, 1H, J=8.3, 2.0 Hz), 6.73 (s, 2H), 4.27 (d, 2H, J=5.9 Hz), 1.12 (s, 9H). MS (m/z) ($^{35}$Cl/$^{37}$Cl) 335/337 (M+1).

Biological Assays

Human mPGES-1 Enzyme Inhibition Assay

Human mPGES-1 (Invitrogen™ (Cat#97002RG, clone ID 6374722)) is subcloned into pcDNA3.1 and transiently expressed in 293E cells. Microsomes are prepared from cell pellets based on published methods (Oullet et al., Purification and characterization of recombinant microsomal prostaglandin E synthase-1, Protein Expression and Purification, 26 pp 489-495 (2002); and Thoren et al., Human Microsomal Prostanglandin E Synthase-1, J. Biol. Chem. 278(25) pp 22199-22209 (2003)). Briefly, pellets are brought up in homogenization buffer (15 mM Tris-HCl, pH 8.0; 0.25 M sucrose; 0.1 mM EDTA; 1 mM glutathione) and sonicated 5×30 seconds on ice. Homogenate is centrifuged at 5000×g for 10 minutes at 4° C. The supernatant fraction is decanted and loaded into Beckman Quick-Seal® tubes and centrifuged at 150,000×g. for 90 minutes at 4° C. The supernatant fraction is discarded by decantation and the pellets are resuspended in assay buffer (10 mM sodium phosphate, pH 7.0; 10% glycerol; 2.5 mM glutathione; Complete Protease Inhibitor Cocktail (Roche)). Protein concentration is determined using the Pierce Coomassie Plus™ reagent.

For the enzyme assay, the microsomes are diluted into assay buffer and 7 μL/well is added to 384 well plates. Compound dilution plates (Nunc Cat#249944) are generated on a Multimek™ and 1 μL/well is added to the assay plates. Prostaglandin H2 ($PGH_2$) is diluted into assay buffer immediately before use and 7 μL/well is added. Final concentrations are 4.4 μg/mL microsomes and 1.69 μM $PGH_2$. After a 2.5 minute incubation at room temperature, 2.5 μL/well of 1 mg/mL $SnCl_2$ in 0.5 N HCl is added to stop the reaction. Five μL of the reaction is transferred to a 384 well plate, acetonitrile (45 μL) containing deuterated $PGE_2$ as an internal standard is added with a Multidrop, and the plates are stored at −20° C. The plates are shipped to Biocius Lifesciences (Wakefield, Mass. 01880) for standard LC/MS analysis for $PGE_2$. The data is used to calculate the $IC_{50}$ (μM). The exemplified compounds inhibit human mPGES-1 with an $IC_{50}$ μM value of <10 μM. Results of three Examples are shown in Table 8. The results demonstrate that the exemplified compounds are potent inhibitors of the mPGES-1 enzyme in an isolated enzyme preparation.

TABLE 8

| Example # | Human mPGES-1 Inhibition, $IC_{50}$ (μM, mean ± std. dev.) |
|---|---|
| 5 | 0.18 ± 0.046 (n = 2) |
| 10 | 0.89 ± 0.35 (n = 2) |
| 14 | 0.24 ± 0.085 (n = 6) |

Cell Based Assay for Measuring Eicosanoid Selectivity

Human epithelial lung carcinoma cell line A549 is obtained from ATCC (CCL-185) and is maintained in Kaighn's F12 ("F12K")+10% fetal bovine serum, (FBS) (plating medium), and 5% $CO_2$. The cells are passaged at 1:3 twice per week.

For assay, cells are released from flasks by washing once with phosphate buffered saline (PBS), then once with Trypsin/EDTA. After 3-5 minutes at 37° C., the cells are suspended in 10 mL of plating medium and centrifuged at 2000 rpm, 25° C., for 5 minutes. The supernatant is aspirated and the cell pellet is resuspended in 10 mL F12K. Cell number is determined by counting an aliquot of cells which has been diluted in PBS and Trypan blue on a hemocytometer. Cells are plated at 40,000/well in 96 well Falcon plates 24 hours prior to treatment. Compounds are diluted in DMSO to 100× of the final concentration in Screen Mates tubes. The medium is removed from the cells and fresh medium (90 μL/well) is added to the cells. The compounds are added at 1 μL/well, n=2, to give seven concentrations each. Cells are pretreated for 30 minutes at 37° C., 5% $CO_2$. Prostaglandin $E_2$ production was induced by the addition of recombinant human interleukin 1β (rhIL-1β) diluted in plating medium to 10× final. A 10 μL/well aliquot is added to give a final rhIL-1β concentration of 0.1-0.2 ng/mL. The treatment period is approximately 18 hours. Conditioned medium is removed to v-bottom polypropylene plates. Serum-free F12K is added to the cells (50 μL/well) along with CellTiter96 reagent (Promega™) (10 μL/well). The plates are incubated at room temperature for 30-45 minutes and then read on a plate reader at A490 to determine viability. A control well receives 10 μL/well 10% Triton X-100 to serve as a toxic control.

The conditioned medium is assayed for levels of $PGE_2$ and $PGI_2$ by specific enzyme immune-assays (EIAs), according to the manufacturer's protocols (Cayman). Briefly, conditioned medium (1 μL) is added to each well of a 96 well plate coated with a capture antibody and containing EIA buffer (49 μL) supplied by the manufacturer. The tracer is diluted with the EIA buffer (50 μL). The detection antibody is diluted with the EIA buffer (50 μL). The plate is covered with adhesive sealing film and is incubated for 1 hour at room temperature on an orbital shaker at 100 rpm. The wash buffer is diluted into Millipore purified water, and the plate is washed 5×350 μL/well, using a plate washer. The substrate (Ellman's reagent) is diluted with Millipore purified water (200 μL/well). After approximately 45 minutes at room temperature on an orbital shaker at 100 rpm, the plates are read at A412 on a plate reader. A standard curve of $PGE_2$ is used to calibrate the unknowns. The exemplified compounds shown in Table 9 inhibit $PGE_2$ formation. The results support that that the Examples inhibit $PGE_2$ synthesis.

TABLE 9

| Example # | $PGE_2$ Inhibition. $IC_{50}$ (μM, mean ± std. dev.) |
|---|---|
| 5 | 0.19 |
| 10 | 2.77 ± 1.51 (n = 3) |
| 14 | 0.87 ± 0.42 (n = 5) |

Human Whole Blood Assay

Blood is collected from normal volunteer donors into sodium heparin vacutainer tubes. Donors are selected, in part, on their confirmation that they have not taken NSAIDs, aspirin, Celebrex, or glucocorticoids within two weeks of the donation. All tubes/donor are pooled into 250 mL Corning conical centrifuge tubes and 436.5 μL/well is distributed into deep well polypropylene plates. Compounds are diluted in DMSO to 100× final and 4.5 μL/well in duplicate or triplicate is added to give 7 point curves. The blood is pretreated at 37° C., 5% $CO_2$, in a humidified atmosphere, loosely covered with a silicone cap mat, for 30 minutes after which 9 μL/well of a solution of 5 mg/mL of lipopolysaccharide (LPS) (Sigma 0111:B4) in 1 mg/mL bovine serum albumin (BSA)/PBS is added to give a final LPS concentration of 100 μg/mL. The plates are incubated for 20-24 hours, loosely covered, at 37° C., 5% $CO_2$, in a humidified atmosphere, on an orbital shaker at approximately 100 rpm. The plates are tightly sealed with the silicone cap mats and are chilled on ice for approximately 1 hour. Then the plates are centrifuged at 1800×g, 10 minutes, 4° C., in an Eppendorf 5810R centrifuge. Plasma is removed from the cell layer using the Rainin L200 with sterile filtered tips and transferred to v-bottom polypropylene plates. One hundred microliters is quantitatively transferred to Costar cluster tubes blocks and 400 μL/well of the methanol stop reagent and internal standards, d-4$PGE_2$, d-4$PGF_{2\alpha}$, and d-4$TX_{2\beta}$ are added. Samples are vortexed for 5 minutes and are placed at −20° C. for at least one hour. Samples are centrifuged for 10 minutes at 4000 rpm in an Eppendorf 5810R.

Solid phase extraction is performed using Waters HLB 30 mg/bed 96 well plates on a vacuum manifold: 1) the matrix is washed with methanol (1 mL), followed by 0.1% formic acid in water (1 mL); 2) 400 μL sample is applied along with 0.1% formic acid in water (900 μL) and allowed to bind for 5 minutes; 3) the matrix is washed with 0.1% formic acid in water (600 μL), followed by 80/20 water/methanol (600 μL); 4) the products are eluted with 2-500 μL volumes of ethyl acetate; 5) the samples are dried under nitrogen and reconstituted in 75/25 water/acetonitrile with 0.1% formic acid (50 μL). The products were analyzed by LC/MS/MS. The Examples listed in Table 10 inhibit $PGE_2$ production. The results support that the Examples inhibit $PGE_2$ synthesis.

TABLE 10

| Example # | $PGE_2$ Inhibition. $IC_{50}$ (μM, mean ± std. dev.) |
|---|---|
| 5 | 0.607 ± 0.502 (n = 3) |
| 10 | 0.792 ± 0.462 (n = 3) |
| 14 | 0.74 ± 0.31 (n = 6) |

The exemplified compounds of the present invention can be readily formulated into pharmaceutical compositions in accordance with accepted practice such as found in Remington's Pharmaceutical Sciences, Gennaro, Ed., Mack Publishing Co. Easton Pa. 1990.

Preferred pharmaceutical compositions can be formulated as a tablet or capsule for oral administration. The tablet or capsule includes a compound of the present invention in an effective amount. The pharmaceutical composition is administered to a patient in amounts effective to treat osteoarthritis, more particularly pain and/or inflammation associated with osteoarthritis. An appropriate amount or dose effective to treat a patient can be determined by a health care provider.

What is claimed is:

1. A compound of the formula below:

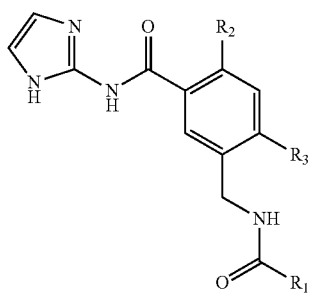

I wherein
R1 is selected from: —$C_{1-5}$ alkyl, —$C(CH_3)_2(OCH_3)$, —$C(CF_3)$-cyclopropyl and —$C(CH_3)$-cyclopropyl;
R2 is selected from: halo, —$CH_3$, —$CF_3$, and —$CHF_2$; and
R3 is selected from: H, halo, and —$CH_3$;
or a pharmaceutically acceptable salt thereof.

2. A compound according to claim 1 wherein R1 is selected from: —$C(CH_3)_3$, —$CH(CH_3)_2$, —$C(CH_3)_2(OCH_3)$, —$C(CF_3)$-cyclopropyl, and —$C(CH_3)$-cyclopropyl; or a pharmaceutically acceptable salt thereof.

3. A compound according to claim 1, wherein R2 is selected from Br, Cl, —$CH_3$, —$CF_3$, and —$CHF_2$, or a pharmaceutically acceptable salt thereof.

4. A compound according to claim 1, wherein R2 is selected from: Cl, —$CF_3$, and —$CHF_2$, or a pharmaceutically acceptable salt thereof.

5. A compound according to claim 1, wherein R3 is selected from: H, F, and —$CH_3$, or a pharmaceutically acceptable salt thereof.

6. A compound according to claim 1, wherein R3 is H or —$CH_3$, or a pharmaceutically acceptable salt thereof.

7. A compound according to claim 1, wherein R3 is H, or a pharmaceutically acceptable salt thereof.

8. A compound which is:

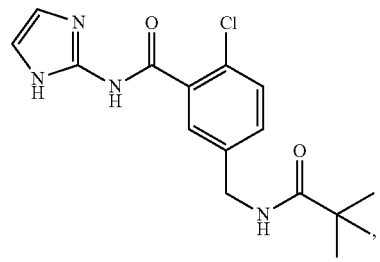

II or a pharmaceutically acceptable salt thereof.

9. A pharmaceutical composition comprising a compound according to claim 1, or a pharmaceutically acceptable salt thereof, and at least one of a pharmaceutically acceptable carrier, diluent or excipient.

10. A method of treating a patient for inflammation from osteoarthritis comprising administering to a patient in need thereof an effective amount of a compound, or a pharmaceutically acceptable salt thereof, according to claim 1.

11. A method of treating a patient for pain from osteoarthritis comprising administering to a patient in need thereof an effective amount of a compound, or a pharmaceutically acceptable salt thereof, according to claim 1.

* * * * *